United States Patent
Bach et al.

(10) Patent No.: US 8,679,082 B2
(45) Date of Patent: Mar. 25, 2014

(54) ADHESIVE WAFER FOR USE IN A COLLECTING DEVICE

(75) Inventors: Anders Bach, Copenhagen S (DK); Danuta Ciok, Nivaa (DK); Esben Stroebech, Hoersholm (DK)

(73) Assignee: Coloplast A/S, Humlebaek (DE)

( * ) Notice: Subject to any disclaimer, the term of this patent is extended or adjusted under 35 U.S.C. 154(b) by 95 days.

(21) Appl. No.: 13/265,344

(22) PCT Filed: Apr. 20, 2010

(86) PCT No.: PCT/DK2010/050088
§ 371 (c)(1),
(2), (4) Date: Oct. 20, 2011

(87) PCT Pub. No.: WO2010/121623
PCT Pub. Date: Oct. 28, 2010

(65) Prior Publication Data
US 2012/0041404 A1 Feb. 16, 2012

(30) Foreign Application Priority Data
Apr. 21, 2009 (DK) .................................. 2009 00515

(51) Int. Cl.
*A61F 5/449* (2006.01)
(52) U.S. Cl.
USPC ........... 604/344; 604/317; 604/327; 604/338; 604/339; 604/343
(58) Field of Classification Search
None
See application file for complete search history.

(56) References Cited

U.S. PATENT DOCUMENTS

| | | | | |
|---|---|---|---|---|
| 5,865,819 A | * | 2/1999 | Cisko et al. | 604/339 |
| 6,626,878 B1 | * | 9/2003 | Leisner et al. | 604/339 |
| 6,709,421 B1 | * | 3/2004 | Falconer | 604/335 |

FOREIGN PATENT DOCUMENTS

| | | |
|---|---|---|
| EP | 0413250 | 2/1991 |
| GB | 2283916 | 5/1995 |
| WO | 2004/087004 | 10/2004 |
| WO | 2007/121744 | 11/2007 |

* cited by examiner

*Primary Examiner* — Jackie Ho
*Assistant Examiner* — Eric Bryant
(74) *Attorney, Agent, or Firm* — Jacobson Holman PLLC

(57) ABSTRACT

Radially divided adhesive wafers are provided for applying to the skins of a human, and which increase the wear time for such adhesive wafers. The adhesive wafer includes a through-going hole for communication with a body opening and an adhesive proximal side for attachment of the wafer to the skin. The adhesive wafer has an inner annular adhesive layer, an outer annular adhesive layer encircling the inner annular adhesive layer, an attachment zone on the distal side of the wafer for attaching a collection bag, and a connecting element for mechanically connecting the first annular adhesive layer to the second annular adhesive layer. The connecting element includes first and second connection areas on the distal side of the respective first and second annular adhesive layers, at least one connection area being radially spaced from the radial edges of the respective annular adhesive layer.

12 Claims, 2 Drawing Sheets

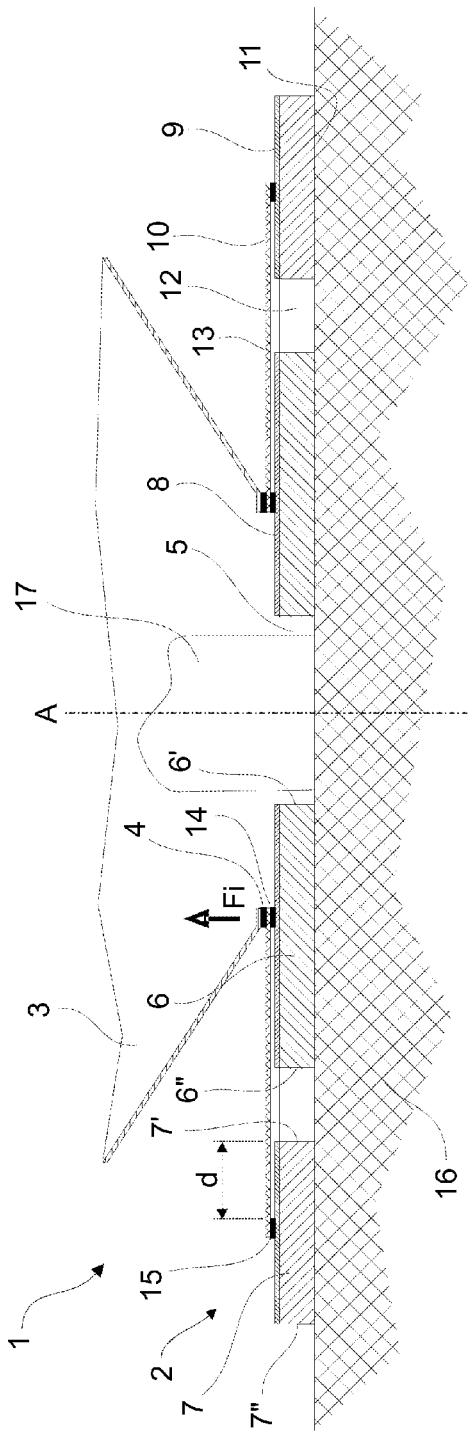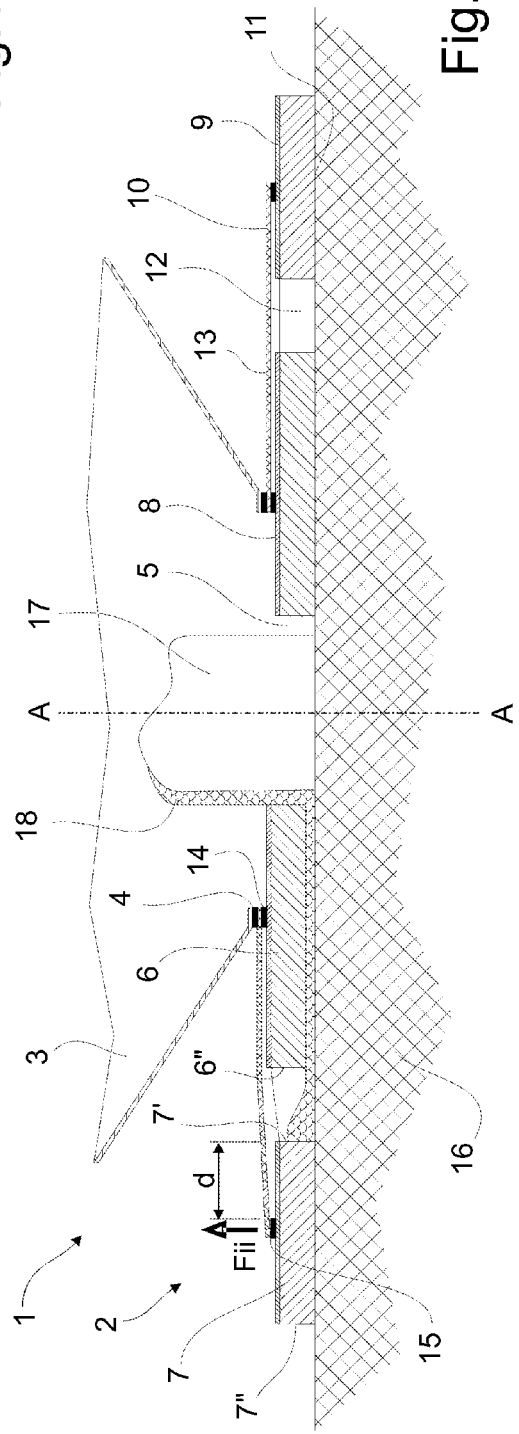

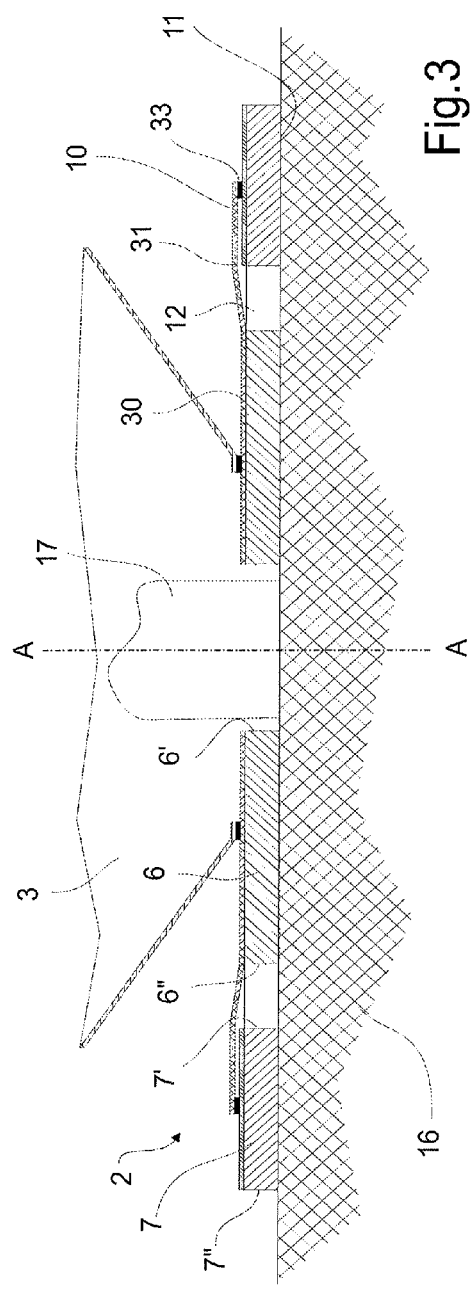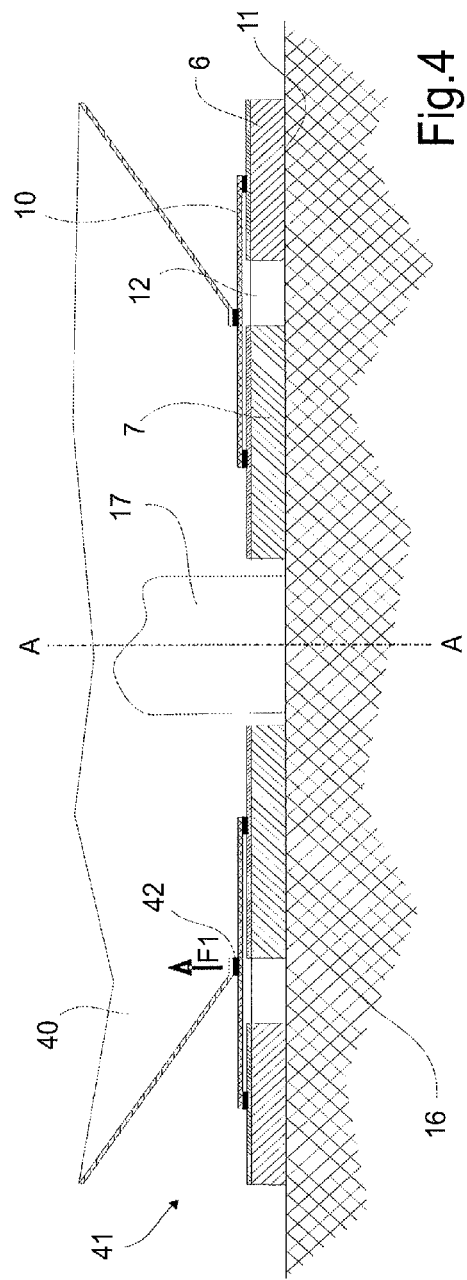

ADHESIVE WAFER FOR USE IN A COLLECTING DEVICE

TECHNICAL FIELD

The current invention relates to radially divided adhesive wafers for applying to the skin of a human, and which increases the wear time of such adhesive wafers.

More specifically, detailed embodiments relating to radially divided adhesive wafers for use in ostomy appliances are described.

BACKGROUND

A major concern for users of collecting devices, such as ostomy devices for collecting fecal output from the stoma, is the occurrence of leakage during wear. Herein, a leakage or leak is understood as being output from a stoma, or other body opening, that works its way in between the skin and the adhesive interface of the ostomy device, all the way from the stoma to the outer periphery of the adhesive wafer. Apart from being unhealthy to the skin that gets in contact with the stoma output, the leak often results in discomfort and potential embarrassing situations for the user.

One way of reducing the risk of leakage is by dividing the adhesive wafer, which attaches the ostomy device to the skin of the user, in a radial inner and a radial outer adhesive layer. The two layers being separated by an opening.

In this way, when a crack starts to propagate between the inner adhesive layer and the skin, the crack will stop when it reaches the opening. A new crack will have to be initiated in the radial outer adhesive layer before leakage can occur. Thus, the opening works as a barrier reducing the risk of leakage occurring, or at least increasing the time for a leakage to occur.

Such a configuration is, for example, known from WO2007/121744.

However, there is still a tendency for a leakage to occur relatively quickly after the inner adhesive layer detaches.

Often, when a leakage occurs, what happens is that a crack is initiated at a weak spot. This crack propagates from the center of the adhesive in a radial direction through the adhesive/skin interface driven by forces between the skin substrate and the adhesive plate. Such forces can originate from body movements and/or from pressure build-up in the collecting bag propagating through the bag wall and cannot be avoided. Throughout the crack propagation, the mode in which the adhesive slips the skin substrate is by way of peeling. Even in two zone adhesives where the adhesive wafer consists of a radially inner and outer adhesive, the forces acting on the adhesive will stay in a crack propagating peel mode, resulting in poor resistance to leakage after initialization of the crack.

When the leak has propagated all the way to the void between the inner and outer adhesive layers, body waste output can flow freely through the leakage. This means that if a pressure is created in the collecting bag this pressure will be transmitted through the leak and into the void. Here, it will generate a peeling force on the radial outer adhesive layer that will propagate quickly through the adhesive/skin interface and all the way to the user's clothes.

BRIEF DESCRIPTION

In one aspect, the invention relates to an adhesive wafer for use in a collecting device for collecting output from a body opening, the adhesive wafer comprising a through-going hole extending axially through the adhesive wafer for communication with the body opening and an adhesive proximal side for attachment of the wafer to the skin surrounding the body opening, wherein the adhesive wafer further comprises, an inner annular adhesive layer,
an outer annular adhesive layer encircling the inner annular adhesive layer,
an attachment zone for attaching a collection bag, provided on the distal side of the adhesive wafer, and
the connection means for mechanically connecting the first annular adhesive layer to the second annular adhesive layer, wherein the connection means comprises a first and a second connection area on the distal side of the respective first and second annular adhesive layers, wherein at least one of the connection areas are arranged in a radial distance from the radial edges of the respective annular adhesive layer.

By providing an adhesive wafer as described, it has been shown that the time before a leakage occurs may be increased. In many cases, the leakage is even prevented. This results in the user being able to wear the adhesive wafer for a longer period of time.

The features described allows for a better control of the distribution of pulling forces which occur in particular as the collecting bag fills up. The control is particularly improved in cases where a crack has propagated between the skin and the inner annular adhesive layer, i.e. the annular adhesive layer closest to the body opening.

By controlling the distribution of pulling forces, it is possible to manipulate the shear and peel forces of the annular adhesive layers. The concept shear and peel forces can best be described through a daily life example: If you want to remove a piece of scotch tape attached to a substrate, you will intuitively start trying to remove it from the ends. In this way, you initiate a crack between the tape and substrate that propagates through the interface when you peel it off. You would not start to remove it from the center of the tape because (besides the fact that it would be difficult to get hold of) the forces needed to remove the tape would be much higher than if you try to peel it from the ends. This is because of the shear resistance in the adhesive that works against removal of the tape. Basically, the applied forces when trying to remove the tape from the center are applied over a larger area of the tape/substrate interface, whereas when you try to peel from the ends the applied forces are concentrated in the peel tip or crack. This way, a much larger force is needed to remove a piece of tape in shear than in peel. E.g., pressure sensitive adhesives (PSA) which are commonly used in ostomy appliances work in this way, i.e. they can hold large forces over their entire area but can be removed easily from the ends through the mechanism of crack propagation.

Thus, in case of a leakage under the inner annular adhesive layer, the device according to this invention will distribute the forces from the static pressure inside the bag on to the center of the outer adhesive layer, i.e. the annular adhesive layer furthest away from the stoma. In this way, the forces on the outer adhesive layer will be in a shear mode instead of a peel mode, making the radial outer adhesive layer much more leak resistant.

Thus, seeing that we arrange the connection area at a distance from the radial edges, it will be arranged in a center part, or close thereto, of the respective annular adhesive layer and will result in a shear force when a pulling force is applied to the connection area.

The transition from peel force to shear forces depends on many factor, e.g. it may depend on the type of adhesive and/or the thickness of the adhesive used. However, in one embodiment it has been shown that for an adhesive wafer for use in an ostomy appliance the attachment of the second annular adhesive layer to the skin is improved where the distance from the radial edges of the second annular adhesive layer to the at least one connection area is at least three times the thickness of the second annular adhesive layer.

In another embodiment of the adhesive wafer it can be considered whether shear forces are dominant. This can for example be determined by a peel test. A reference test is done where the connection area is provided at the periphery of the test adhesive which can e.g. be an adhesive wafer for an ostomy appliance. A 90° peel force is applied to the connection area and the force required to remove the test adhesive from a steel substrate at 5 mm/s at 23° C. is considered the reference peel force. Subsequently the connection area is moved in the radial direction and the test is repeated. When the peel force is equal to or above twice the value of the reference peel force, shear forces are considered dominant.

Thus, in some embodiments at least one of the connection areas are arranged in a radial distance from the radial edges wherein shear forces are dominant.

Moreover, seeing that the outer annular adhesive layer encircles the inner annular adhesive layer, an opening can be provided by dimensioning the radial distance to the first outer radial edge smaller than the radial distance to the second inner radial edge. The opening between the first and the second annular adhesive layers functions as a buffer and/or barrier for output from the stoma when this has propagated through the inner annular adhesive layer. The radial extent of such an opening can be anything from a few millimeters to several centimeters, depending upon its function and the buffer capacity desired.

The term 'annular' should be understood as an element which forms a loop, for example a rubber band. However, as for a rubber band, no specific shape should be read into the term, as the annular adhesive layers may still be functional having many different shapes, such as triangular, rectangular or circular. Many other irregular shapes could also be envisioned.

Furthermore, unless otherwise specified, any reference to a radial or axial dimension should be understood with reference to the central axis of the through-going hole.

In one embodiment the inner annular adhesive layer comprises a first inner radial edge, defining the through-going hole, and a first outer radial edge, the first inner radial edge and the first radial outer edge defining the radial extent of the inner annular adhesive layer, and the outer annular adhesive layer comprises a second inner radial edge, with a radius larger than the first radial outer edge, whereby the outer annular adhesive layer encircles the inner annular adhesive layer, and a second outer radial edge, the second inner radial edge and the second radial outer edge defining the radial extent of the outer annular adhesive layer.

In some embodiments, the attachment zone for attaching the collecting bag is arranged on the distal side of the inner annular adhesive layer. However, in alternative embodiments it may also be arranged on the distal side of the outer annular adhesive layer.

In one embodiment, the connection means are provided as an annular film, attached to the distal side of the inner adhesive layer in the first connection area and to the distal side of the outer adhesive layer in the second connection area. Such a film will typically have flexible characteristics allowing the adhesive wafer to follow the contour of the skin surface, while at the same time providing a secure mechanical connection between the annular adhesive layers. Thus, an adhesive wafer which is comfortable to wear can be provided.

In one embodiment, the annular film is in the shape of a first backing layer whereon the inner adhesive layer is disposed, the first backing layer having a radially extending section overlapping the outer annular adhesive layer, and wherein at least a part of the radially extending section is attached to the outer annular adhesive layer in the connection area.

Typically, the annular adhesive layers will be disposed on backing layers. This facilitates handling during production as direct handling of many types of adhesives may deform or tear the adhesive due to its viscosity and cohesion. Thus, by using one of the backing layers of the annular adhesive layers as the annular film an easy and simple way to connect the two annular adhesive layers to each other can be provided.

It should of course be understood, that backing layers can be provided on each annular adhesive layer where a separate annular film is connected, e.g. by welding, to the respective backing layer.

In some cases it may be desirable to monitor the opening between the two annular adhesive layers in order to see if any output from the body opening is present indicating that the adhesive wafer should be changed in order to avoid output propagating further through the outer annular adhesive layers and thereby creating a leak. In such cases, the annular film may be transparent.

In one embodiment, the attachment zone can be provided on the annular film. This will distribute the pulling force from the collecting bag to the connection area on both the inner annular adhesive layer and the outer annular adhesive layer.

However, other embodiments where the attachment zone is provided on the distal side of the inner annular adhesive layer may be arranged, e.g. on the first backing film, on which the collecting bag may be welded or glued.

Alternatively, the attachment zone can be provided on the distal side of the outer annular adhesive layer.

The adhesive wafer as described can be used in different applications where output from a body opening is to be collected. Thus the adhesive wafer can be used in an ostomy appliance where an ostomy bag is attached to the attachment zone.

The ostomy pouch can, for example, be welded to the adhesive wafer in the attachment zone. Alternatively, the ostomy pouch can be releasably coupled to the adhesive wafer in the attachment zone. This can, for example, be done by using known mechanical or adhesive two-piece coupling systems such as the Easiflex® or Assura® ostomy systems produced by Coloplast A/S.

The annular adhesive layers will typically consist of an adhesive based on hydrocolloid, acrylic, silicone or other generally known skin friendly adhesive.

BRIEF DESCRIPTION OF THE DRAWINGS

By way of example, a number of embodiments will hereby be further described, wherein identical reference numbers have been used for similar components.

FIGS. 1 and 2 show, in section along the axis A-A, one embodiment of an adhesive wafer, FIG. 3 shows a second embodiment of an adhesive wafer, and FIG. 4 shows a third embodiment of an adhesive wafer.

DETAILED DESCRIPTION

A first embodiment of an ostomy appliance 1 is shown in section in FIGS. 1 and 2.

The ostomy appliance 1 is formed of an adhesive wafer 2, to which an ostomy bag 3 is attached by a first annular weld 4.

A through-going hole 5 extends longitudinally along axis A-A through the adhesive wafer 2. As can be seen, the ostomy bag 3 is attached around the through-going hole 5 in order to allow material entering the through-going hole to be collected in the ostomy bag.

The adhesive wafer 2 is formed of a first annular adhesive layer 6 and a second annular adhesive layer 7. The first and second annular adhesive layers 6,7 extend radially (i.e. perpendicularly to the longitudinal axis A-A of the through-going hole) between a first and a second inner radial edge 6',7' and a first and a second outer radial edge 6",7" which define the radial extent of the respective annular adhesive layers.

As can be seen, the first outer radial edge 6" has a smaller radius from the axis A-A than the second inner radial edge 7', resulting in the second annular adhesive layer 7 encircling the first annular adhesive layer 6 when the two annular adhesive layers are arranged in the same plane and co-axially around the longitudinal axis A-A.

Furthermore, such dimensioning will also create an annular opening 12 between the first and the second annular adhesive layers 6,7.

The first and the second annular adhesive layers 6,7 are disposed on respective first and second backing layers 8,9. Such backing layers facilitate manufacturing of the adhesive wafers, as the annular adhesive layers are easier to control when disposed thereon. Moreover, the first and second backing layers prevent the annular adhesive layers from adhering on the distal side 10 (i.e. the side facing away from the user during use) of the adhesive wafer, so they only adhere on the proximal side 11 of the adhesive wafer.

An annular film 13 connects the first annular adhesive layer 6 to the second adhesive layer 7. The annular film 13 is mechanically connected, e.g. by welding or gluing, to the first backing layer 8 by an inner annular weld 14 and to the second backing layer 9 by an outer annular weld 15. The annular film thereby holds the first and the second annular adhesive layers in place with respect to each other and allows only minor displacement which mainly occur in the longitudinal direction along axis A-A. Further, a leakage from the receiving hole under the inner adhesive 6 can be contained by the outer adhesive 7 and the connecting film 13.

During use, the ostomy appliance 1 is attached to the skin 16 of a user allowing a stoma 17 to be arranged in the through-going hole 5, so that output from the stoma enters the ostomy bag 3.

The ostomy appliance 1 is, in one example, applied by first cleaning the skin onto which it is to be attached. The through-going hole 5 may be cut wider and/or cut into a shape to allow the stoma 17 to pass through it. Then, a release liner (not shown) covering the adhesive proximal side of the adhesive wafer is removed and the ostomy appliance is adhered to the skin 16. In case the through-going hole 5 is larger than the stoma, a paste (not shown) may be used to fill out gap between the stoma and the first inner radial edge 6' of the first annular adhesive layer 6.

FIG. 1 illustrates a freshly applied ostomy appliance 1 as described above. When fecal matter exits the stoma 17, it will thus fall into ostomy bag 3. As matter enters the ostomy bag, the bag will begin pulling in the attachment to adhesive wafer. In the current example such pulling will occur at the first annular weld 4. This results in a pulling force component $F_i$.

However, over time output 18 from the stoma may in some cases seep between the stoma and the first inner radial edge 6' and continue in between the first annular adhesive layer 6 and the skin 16. In time the output 18 may seep into the annular opening 12, as is illustrated in FIG. 2.

If the ostomy appliance is left on for much longer the output may eventually continue in between the second annular adhesive layer 7 and the skin 16 and into the ambient environment. This will result in a leakage which is very unpleasant to the user.

However, by providing the annular opening 12 the leakage may be prevented for a while longer, as it is the initial separation of the respective annular adhesive layer 6,7 from the skin that takes time. Once this initial separation has occurred, a path will typically relatively quickly be generated from the respective first and second inner radial edges 6', 7' and out between the skin and the remaining adhesive.

Moreover, by providing the annular film 13 in a transparent material it is possible for the user to observe when output 18 enters the annular opening 12. The user then knows that it is time to change the ostomy appliance.

As the first annular adhesive layer 6 separated from the skin 16, the pulling force from the ostomy bag is transferred through the annular film 13 to the outer annular weld 15. This results in a pulling force component $F_{ii}$ at the outer annular weld 15.

As can be seen from FIGS. 1 and 2, the outer annular weld 15, and thereby the point of pulling, is arranged in a radial distance 'd' from the second inner radial edge 7'. By arranging the point of pulling away from the edge of the adhesive layer, a shear force is obtained, i.e. the force is distributed through the adhesive to a large surface area between the annular adhesive layer and the skin. This reduces the risk that the adhesive layer separates from the skin. If the pulling point (outer annular weld 15) was arranged at the second radial edge 7' the pulling force would extend straight through with minimal distribution and thereby create a high pull force in one point resulting in a higher risk of separation. In other words, this would result in a peel force, creating a weak peel front.

FIG. 3 shows an alternative embodiment of an ostomy appliance, wherein similar parts have been given the same reference numbers as referred to in FIGS. 1 and 2 above.

As can be seen, a third backing layer 30 whereon the inner annular adhesive layer 6 is disposed has a radially extending section 31 which extends radially beyond the first outer radial edge 6". The extending section overlaps the outer annular adhesive layer 7 and is connected to the second backing layer by an outer weld 33.

Yet another embodiment is shown in FIG. 4 where similar parts have been given the same reference numbers as in previous illustrations.

An ostomy bag 40 is attached to the adhesive wafer 41 at an attachment zone provided by a center weld 42 on the annular film 13. The center weld is arranged radially between the inner and outer annular weld 14,15. Thus, when a pulling force $F_1$ is exerted by the bag on the adhesive wafer, it is distributed evenly via the annular film 13 to the respective inner and outer annular weld 14, 15 and from there distributed through the inner and outer annular adhesive layers.

It should be understood that the above detailed embodiments are examples only, and many other configurations and combinations may be envisioned within the scope of the present invention.

For example, the ostomy appliance described above can be other types of collecting devices for receiving output from a body opening. Such other devices could be a urine collection device or a device for fecal management, i.e. arranged at the rectum of a user experiencing fecal incontinence. Thus, when referring to ostomy appliances and parts thereof (in particular the adhesive wafer), and stomas and output from them, a person skilled in the art will understand that the teachings herein may be generalized to collecting devices and parts thereof (in particular the adhesive wafer), and body openings and output from them.

REFERENCE NUMBERS 1. ostomy appliance
2. adhesive wafer
3. ostomy bag
4. first annular weld
5. through-going hole
6. first annular adhesive layer
6'. first inner radial edge
6". first outer radial edge
7. second annular adhesive layer
7'. second inner radial edge
7". second outer radial edge
8. first backing layer
9. second backing layer
10. distal side of the adhesive wafer
11. proximal side of the adhesive wafer.
13. annular film
14. inner annular weld
15. outer annular weld
16. skin
17. stoma
18. output
30. third backing layer
31. radially extending section
33. outer weld
40. ostomy bag
41. adhesive wafer
42. center weld

The invention claimed is:

1. An adhesive wafer for use in a collecting device adapted for collecting output from a body opening, the adhesive wafer including a through-going hole extending axially through the adhesive wafer for communication with the body opening and an adhesive proximal side for attachment of the adhesive wafer to the skin surrounding the body opening, the adhesive wafer comprising:
   a first backing layer and a second backing layer;
   an inner annual adhesive layer;
   an outer annular adhesive layer encircling the inner annular adhesive layer;
   the inner and the outer annular adhesive layers being disposed on said first and second backing layers, respectively;
   an attachment zone provided on a distal side of the adhesive wafer for attaching a collection bag; and
   a connection means for mechanically connecting the inner annular adhesive layer to the outer annular adhesive layer, said connection means including a first and a second connection area on the distal side of the respective inner and outer annular adhesive layers, at least one of the first and second connection areas being radially spaced away by a radial distance from radial edges of the respective inner and outer annular adhesive layer.

2. The adhesive wafer according to claim 1, wherein the inner annular adhesive layer includes a first inner radial edge, defining the through-going hole, and a first radial outer edge, the first inner radial edge and the first radial outer edge defining the radial extent of the inner annular adhesive layer, and
   the outer annular adhesive layer includes a second inner radial edge with a radius larger than the first outer radial edge, whereby the outer annular adhesive layer encircles the inner annular adhesive layer, and a second outer radial edge, the second inner radial edge and the second outer radial edge defining the radial extent of the outer annular adhesive layer.

3. The adhesive wafer according to claim 1, wherein the radial distance from the first outer radial edge and second outer radial edge of the respective inner and outer annular adhesive layer is at least three times a thickness of the respective inner and outer annular adhesive layer.

4. The adhesive wafer according to claim 1, 2, or 3, wherein at least one of the first and second connection areas are arranged such that the radial distance from the radial edges is located where shear forces are dominant.

5. The adhesive wafer according to claim 1, wherein the attachment zone is arranged on the distal side of the inner annular adhesive layer.

6. The adhesive wafer according to claim 1, wherein the connection means is provided as an annular film, attached to the distal side of the inner adhesive layer in the first connection area and to the distal side of the outer adhesive layer in the second connection area.

7. The adhesive wafer according to claim 6, wherein the annular film is in the shape of the first backing layer whereon the inner adhesive layer is disposed, the first backing layer having a radially extending section overlapping the outer annular adhesive layer, and wherein at least a part of the radially extending section is attached to the outer annular adhesive layer in the second connection area.

8. The adhesive wafer according to claim 6, wherein the annular film is transparent.

9. The adhesive wafer according to claim 6, wherein the attachment zone is provided on the annular film.

10. An ostomy appliance comprising:
    an adhesive wafer including a through-going hole extending axially through the adhesive wafer adapted for communication with a body opening and an adhesive proximal side for attachment of the wafer to the skin surrounding the body opening, the adhesive wafer including,
    a first backing layer and a second backing layer;
    an inner annular adhesive layer;
    an outer annular adhesive layer encircling the inner annular adhesive layer;
    the inner and the outer annular adhesive layers being disposed on said first and second backing layers, respectively;
    an attachment zone provided on a distal side of the adhesive wafer for attaching a collection bag; and
    a connection means for mechanically connecting the inner annular adhesive layer to the outer annular adhesive layer, said connection means including a first and a second connection area on the distal side of the respective inner and outer annular adhesive layers, at least one of the first and second connection areas being radially spaced away by a radial distance from radial edges of the respective inner and outer annular adhesive layer; and
    an ostomy pouch attachable to the adhesive wafer.

11. The ostomy appliance according to claim 10, wherein the ostomy pouch is welded to the adhesive wafer in the attachment zone.

12. The ostomy appliance according to claim 10, wherein the ostomy pouch is releasably coupled to the adhesive wafer in the attachment zone.

* * * * *